(12) United States Patent
Levine

(10) Patent No.: US 8,215,954 B2
(45) Date of Patent: Jul. 10, 2012

(54) METHODS FOR EFFECTING ORAL TREATMENT OF TEETH OR GUMS

(76) Inventor: Jonathan B. Levine, Purchase, NY (US)

( * ) Notice: Subject to any disclaimer, the term of this patent is extended or adjusted under 35 U.S.C. 154(b) by 0 days.

(21) Appl. No.: 12/726,770

(22) Filed: Mar. 18, 2010

(65) Prior Publication Data

US 2011/0104631 A1    May 5, 2011

Related U.S. Application Data

(63) Continuation-in-part of application No. 12/186,641, filed on Aug. 6, 2008, now Pat. No. 8,029,278.

(51) Int. Cl.
*A61C 3/00* (2006.01)
*A61C 5/00* (2006.01)

(52) U.S. Cl. .................................. 433/29; 433/215
(58) Field of Classification Search ............... 433/29, 433/215
See application file for complete search history.

(56) References Cited

U.S. PATENT DOCUMENTS

| | | | |
|---|---|---|---|
| 5,702,250 A | 12/1997 | Kipke | 433/37 |
| 6,155,832 A | 12/2000 | Wiesel | |
| 6,162,055 A | 12/2000 | Montgomery et al. | |
| 6,616,451 B1 | 9/2003 | Rizolu et al. | |
| 6,733,290 B2 | 5/2004 | West et al. | 433/29 |
| 6,752,627 B2 | 6/2004 | Lin | |
| 6,783,363 B2 | 8/2004 | Eguchi et al. | |
| 6,893,259 B1 * | 5/2005 | Reizenson | 433/29 |
| 6,902,397 B2 | 6/2005 | Farrell et al. | |
| 7,004,756 B2 | 2/2006 | Andersen | |
| 7,086,862 B2 | 8/2006 | Craig | |
| 7,144,249 B2 | 12/2006 | Rizoiu et al. | |
| 7,160,111 B2 | 1/2007 | Baughman | |
| 7,223,270 B2 | 5/2007 | Altshuler et al. | |
| 7,250,155 B2 | 7/2007 | Yamaguchi et al. | |
| 2001/0044096 A1 * | 11/2001 | Lindquist | 433/215 |
| 2004/0193236 A1 | 9/2004 | Altshuler et al. | |
| 2005/0053898 A1 | 3/2005 | Ghosh et al. | |

(Continued)

FOREIGN PATENT DOCUMENTS

CA    2319890    3/2001

OTHER PUBLICATIONS http://www.exit15.com/briteteeth-laser-light-home-teeth-whitening "Sunshine Smiles Brite-Teeth Laser Light Home Teeth Whitening" p. 760 Nov. 15, 2007.

(Continued)

*Primary Examiner* — John J Wilson
(74) *Attorney, Agent, or Firm* — H. Jay Spiegel

(57) ABSTRACT

A method for effecting an oral treatment of teeth and/or gums using an intra-oral device that has a mouthpiece in which is embedded a flexible circuit board and arrays of spaced apart lamps. The mouthpiece has a curvature. The lamps may be light emitting diodes that generate electromagnetic radiation, preferably in the white and blue light spectrum and the infrared and ultraviolet light spectrum. The arrays are positioned to expose the facial and lingual sides of the teeth and/or gums for effecting the treatment when the mouthpiece is positioned to fit upper and lower rows of teeth within accommodating recesses. The flexible circuit board is flexed to exhibit a curvature that follows a curvature of the mouthpiece. Treatments include whitening teeth, desensitizing teeth, and treating gums to prevent periodontal disease.

19 Claims, 7 Drawing Sheets

U.S. PATENT DOCUMENTS

| | | |
|---|---|---|
| 2005/0064370 A1 | 3/2005 | Duret |
| 2005/0074717 A1 | 4/2005 | Cleary et al. .................... 433/24 |
| 2005/0158687 A1 | 7/2005 | Dahm ............................. 433/29 |
| 2005/0172429 A1 | 8/2005 | Russell et al. |
| 2005/0202363 A1 | 9/2005 | Osterwalder ................... 433/29 |
| 2005/0231983 A1 | 10/2005 | Dahm ............................ 362/800 |
| 2006/0019214 A1 | 1/2006 | Lawrence et al. .............. 433/29 |
| 2006/0141422 A1 | 6/2006 | Philp et al. |
| 2006/0154209 A1* | 7/2006 | Hayman et al. .............. 433/215 |
| 2006/0194164 A1 | 8/2006 | Altshuler et al. |
| 2006/0257822 A1 | 11/2006 | Ghosh et al. |
| 2006/0281042 A1* | 12/2006 | Rizoiu et al. ................... 433/29 |
| 2007/0003905 A1 | 1/2007 | Nguyen et al. ................ 433/215 |
| 2007/0009856 A1* | 1/2007 | Jones et al. ................... 433/215 |
| 2007/0015112 A1 | 1/2007 | Hochman et al. |
| 2007/0020584 A1 | 1/2007 | Madray |

OTHER PUBLICATIONS http://www.perfectlywhite.com/ "Welcome to Perfectly White.com (online since 2004)".

Smile Teeth Whitening Systems, 2005-2006 http://www.smileteeethwhitening.com/asupplies.html.

\* cited by examiner

US 8,215,954 B2

METHODS FOR EFFECTING ORAL TREATMENT OF TEETH OR GUMS

CROSS REFERENCE TO RELATED APPLICATION

This application is a continuation-in-part of U.S. patent application Ser. No. 12/186,641 filed Aug. 6, 2008, now U.S. Pat. No. 8,029,278, incorporated by reference herein.

BACKGROUND OF THE INVENTION

1. Field of the Invention

The present invention relates to methods for effecting an oral treatment of teeth or gums using mouthpiece containing lamps to expose electromagnetic radiation to effect the oral treatment. For instance, the exposure could be to an adhesive whitening gel to whiten teeth. Alternatively, it may be to kill harmful bacteria in the mouth or on or around the gums by exposure to the electromagnetic radiation and thereby prevent periodontal disease. Another oral treatment that can be effected by the exposure of electromagnetic radiation is desensitizing teeth.

2. Description of Related Art

Tooth whitening in the dental office takes up to 2 hours, expensive, is painful and the results will start to regress as early as 7 days after the treatment. Most over-the-counter products are messy, can burn the fingers and the results usually take 7-10 days to see minimal improvement. The consumer needs a customizable whitening approach that gives the same results from professional whitening but at the convenience of the home and with much less money.

Whitening is governed by the concentration of the whitening active and the contact time (i.e., the time the whitening agent is on the teeth). Whitening results are best achieved when there is high frequency of the whitening agent in a safe way and without the need of high concentration whitening agents that can burn the tissue. By increasing the frequency of the whitening by giving the consumer the ability to whiten at home, the regression phenomenon seen with the professional whitening will be eliminated.

It is desired to provide a whitening device that is coupled with a delivery system of the whitening gel and an adhesive that keeps hydrogen peroxide targeted to the area to whiten. Such a whitening device preferably causes no harmful breakdown by-products, and is delivered in a single dose and hygienic way.

In addition, harmful bacteria is responsible for causing gum disease in the mouth. Specifically, the gram negative anaerobic bacteria is responsible. However, such bacteria is killed off from ultraviolet light exposure. It would therefore be desirable for a consumer to expose such bacteria to ultraviolet light on their own without relying on the assistance of professional help to do so.

SUMMARY OF THE INVENTION

One aspect of the invention resides in a method to treat teeth and/or gums using an intra-oral device that is partly inserted into a user's mouth to create a light and/or heat effect to cause a reaction or increase a reaction rate of a light and/or heat sensitive material to teeth or gums and thereby effect an oral treatment.

A more specific aspect of the invention resides in an intra-oral whitening device including a mouthpiece and that is suited to create a whitening and heat effect to increase a reaction rate of a photosensitive agent, i.e., hydrogen peroxide gel, previously applied to the teeth. The person whose teeth are to be whitened can wear the device, i.e., insert the mouthpiece into their mouth, and whiten his/her teeth without the need of a professional office and is safe, effective and convenient.

In the past, the best whitening results have been done in the professional office that is expensive and time consuming. The intra oral whitening device of the present invention may allow consumers to whiten their teeth in the convenience of their home, to customize the whitening procedure for their own needs and to do so safely and effectively without the need for a dentist.

It is a further aspect of the invention to expose harmful bacteria in the mouth to electromagnetic radiation, such as ultraviolet light, to kill the harmful bacteria in an effort to halt gum disease caused by such bacteria, e.g., the gram negative anaerobic bacteria.

BRIEF DESCRIPTION OF THE DRAWING

For a better understanding of the present invention, reference is made to the following description and accompanying drawings, while the scope of the invention is set forth in the appended claims:

DETAILED DESCRIPTION OF THE INVENTION

Figure 1:
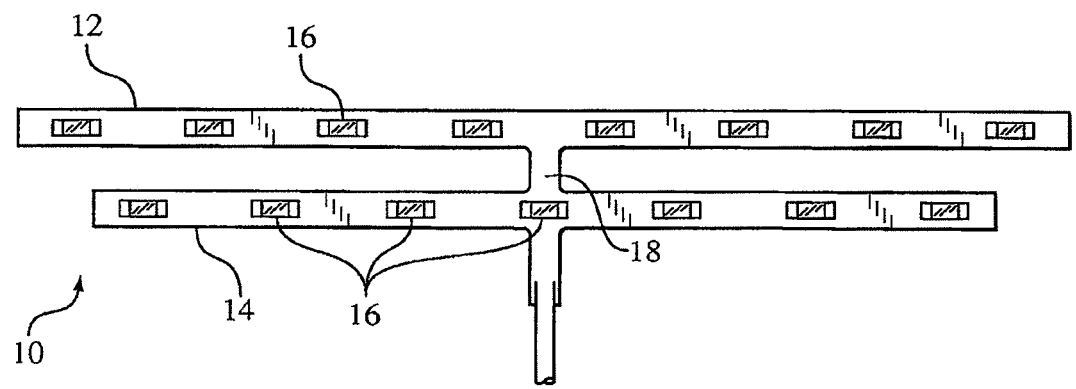
FIG. 1 is a plan view of a flexible circuit board extending in a plane in accordance with the invention.

Turning to the drawing, FIG. 1 shows a flexible circuit board 10 with dual parallel arrays 12, 14 of ultraviolet light emitting diode (UV LED) lamps 16 in accordance with the invention. The circuit board 10 has a central connecting strip 18 that extends between the dual parallel arrays 12, 14 at a generally central location. The flexible circuit board 10 is flexed to form a curvature as part of an intra-oral device 20 of FIG. 3.

Figure 2:
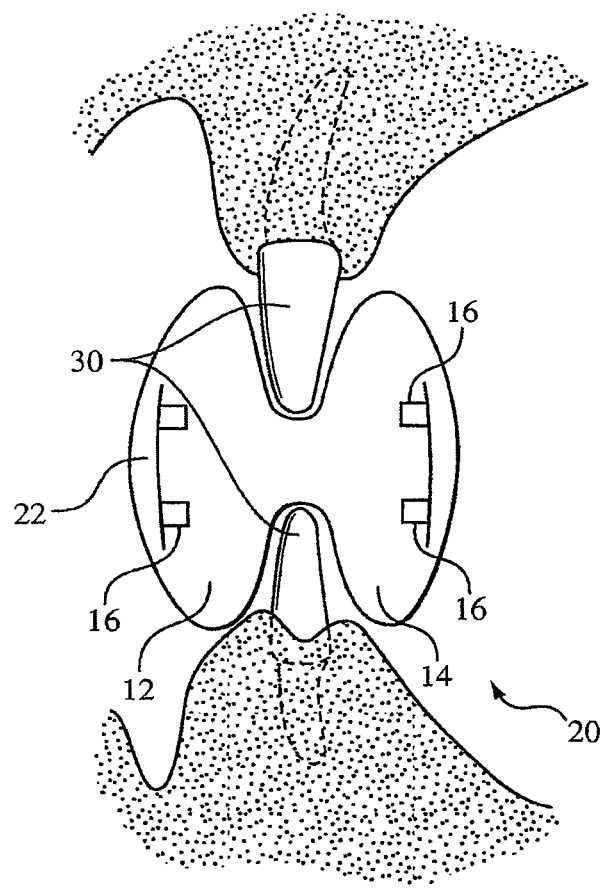
FIG. 2 is a cross-section of a mouthpiece in accordance with the invention in position to whiten teeth or effect another oral treatment to the teeth or gums through exposure to electromagnetic radiation emitted from lamps that are embedded in the mouthpiece.
Figure 3:
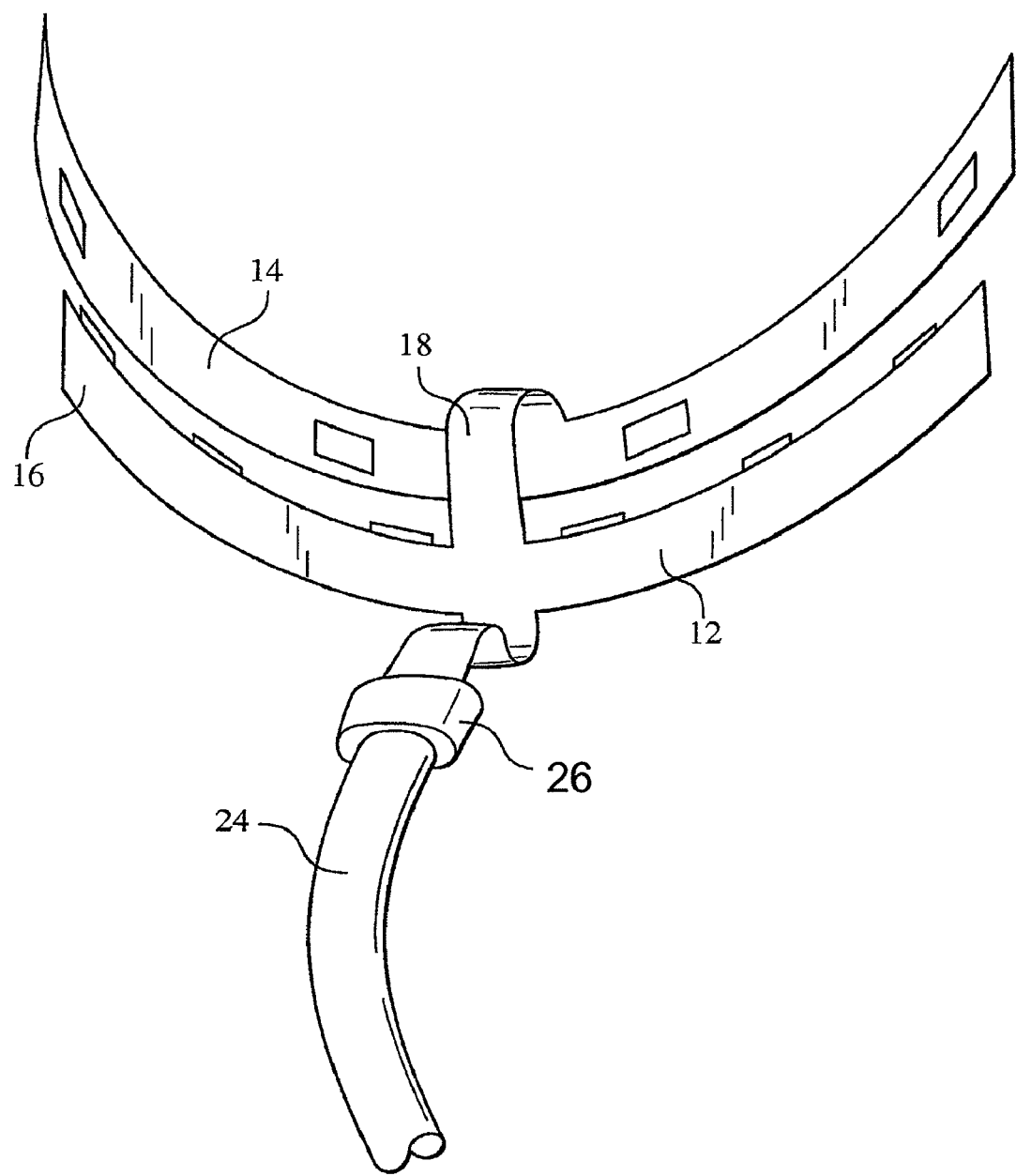
FIG. 3 is an isometric view of the flexible circuit board in a flexed, curved configuration in accordance with the invention and also showing the location of lamps, power cord and socket and plug connection.

Starting from the planar orientation of the flexible circuit board 10 shown in FIG. 1, the circuit board 10 is folded or flexed at the central connecting strip 18 so that the respective arrays 12, 14 of lamps 16 are opposed to each other in the manner shown in FIGS. 2 and 3. The circuit board 10 is then curved in the manner shown in FIG. 3. These two steps help in the positioning of the LED lamps 16 on both the facial and lingual sides of the teeth to be treated, as shown in FIG. 2. That is, such position is realized upon positioning part of the assembly, i.e. a mouthpiece 22 containing the arrays 12, 14 of lamps 16, within the mouth of a person whose teeth are to be whitened, or otherwise treated.

The intra-oral device 20 of FIGS. 2 and 3 is preferably made of moldable, flexible, plastic that exposes both arches, upper and lower, to the EM radiation in the 300-990 nm range and heat less than about 52 degrees centigrade. When used for whitening teeth, the combination of the plastic device, light and heat, adhesive whitening gel all together will create effective whitening that takes much less time than conventional whitening techniques and is safe and effective.

The lamps 16 serve as light sources and are preferably LED lamps with a high concentration in the white and blue and the non-visible light spectrum (infrared and UV), which is known to form highly effective bleaching ions when exposed to the unseen portion of the spectrum. The light sources are preferably embedded into a moldable, flexible plastic mouthpiece 22 on grids that surround the upper and lower front surfaces of the teeth with the necessary light along with heat that has two or three levels stopping at about 52 degree Centigrade to avoid pulpal sensitivity. The plastic mouthpiece 22 is preferably made from a transparent or translucent material.

Figure 4:
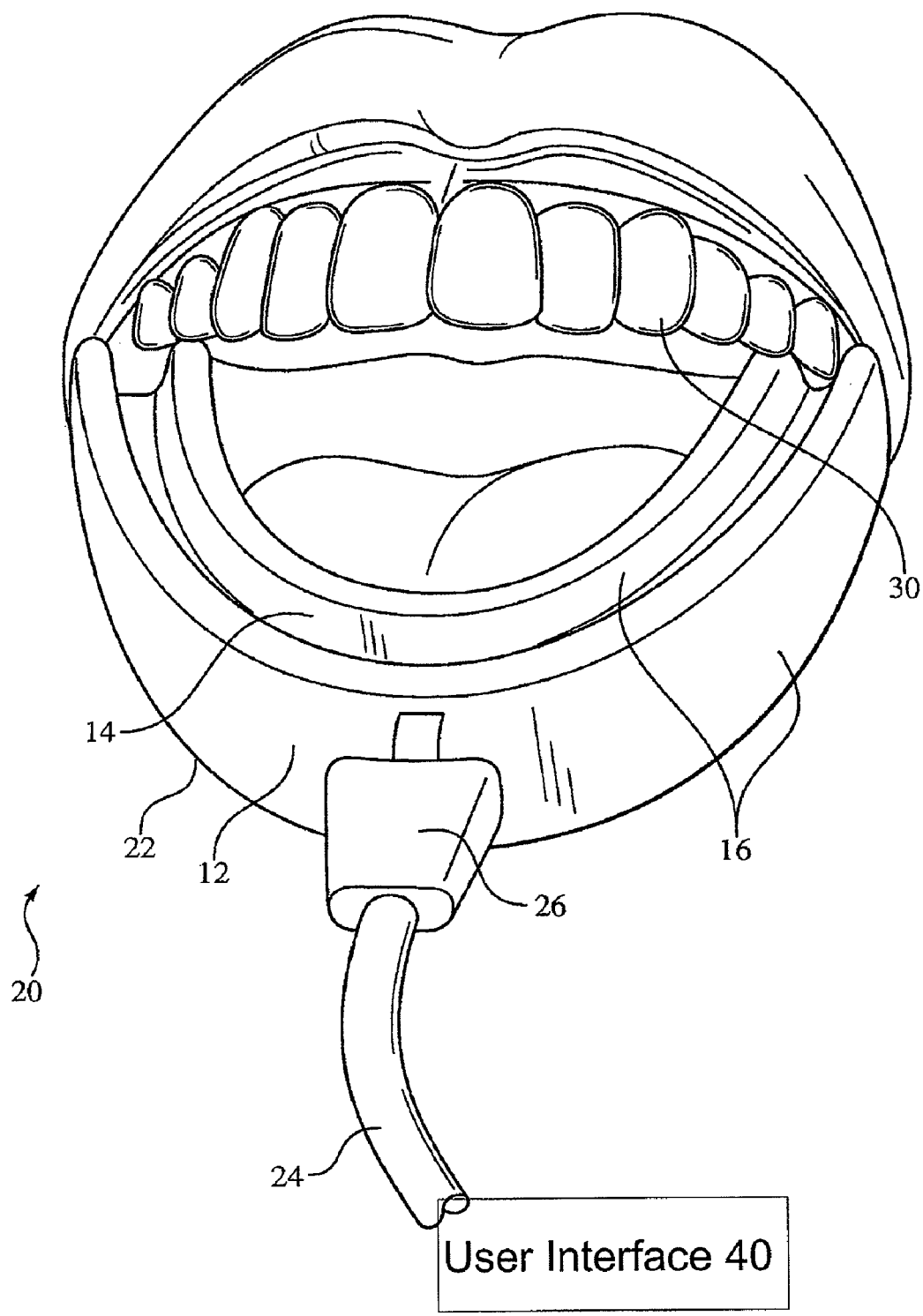
FIG. 4 is an isometric view of the mouthpiece being positioned in a person's mouth wherein the mouthpiece embeds the curved flexible circuit board of FIG. 3 as well as the lamps, and the power cord and the socket and plug connection are also depicted.

The lamps 16 may be positioned along a full length of the flexible circuit board, inclusive of the curvature of the flexed circuit board 10 at the base of the U-shape it has within confines of the mouthpiece 22 (see FIGS. 3 and 4). The curvature of the flexible circuit board 10 generally follows the curvature of the mouthpiece 22.

Turning to FIG. 2, the LED lamps 16 shine on both upper and lower teeth 30 substantially equally as the patient (whose mouth contains the mouthpiece 22 of the intra-oral device 20) closes down the mouth. The mouthpiece 22 has a generally H-shaped cross section with upper and lower recessed portions to respectively accommodate therein the upper and lower rows of teeth 30 to be treated (see FIG. 2). The recessed portions, or grooves, are defined between the sides of the H-shaped mouthpiece 22 with at least one array of lamps 16 being arranged on each side of the H-shaped mouthpiece 22. As shown in FIG. 2, the lamps 16 are oriented to direct electromagnetic radiation toward one another so that when teeth 30 or gums are positioned in the grooves, the array 12 of lamps 16 applies heat and/or light to the facial side of the teeth 30 or gums while the array 14 of lamps applies heat and/or light to the lingual side of the teeth 30 or gums.

The power supply may be intra-oral or extra-oral and would be advantageous if the consumer can customize the oral treatment by dialing the level of heat and light, such as by choosing as many as two or three light and heat intensities. The power supply may use a power cord 24 to provide power via a plug and socket connection 26 with the flexible circuit board 10. An end of the cord 24 may have the plug, and the circuit board 10 may have the socket or vice versa. The power cord 24 may include a user interface 40 at an intermediate position, as shown in FIG. 4, and the user interface enables the person to select a plurality of light intensities that the lamps 16 are to radiate during their operation and/or an amount of heat to be generated by the lamps 16 during their operation. The user interface 40 is spaced apart from the mouthpiece 22.

Turning to FIG. 3, the central positioning also inherently provides treatment of biting surfaces of teeth 30, such as for purposes of changing a condition of the biting surfaces for the better as a result of prolonged exposure to electromagnetic radiation from the lamps. The inherent light piping quality of the materials appropriate for use in the mouthpiece of the present invention enhances with lensing or reflective films.

A headset may be provided that uses the technology of T-ink, the use of printed technology that takes the circuit board and incorporates this into the printed design eliminating buttons, wires and switches. The user interface may be incorporated into the headset.

The headset gives an interactive component to the user, explain the use of the device, offer important instructions and they can get key learnings from the doctor, and can set up a music timer to the headset.

As an alternative to the headset, any handheld device may be used with appropriate control buttons and may be small enough to fit in a shirt pocket or held to one's blouse with a clip. This enables hands free operation while the lamps are operating.

FIGS. 5-8 illustrate three approaches intended to direct electromagnetic radiation such as light evenly across tooth faces. The light travels along a light path in which the light changes direction. After leaving the light emitting diode, the light strikes an angled mirror surface to be diverted toward reflective surfaces that in turn reflect the light toward the tooth faces. Such a light path is analogous to the path taken by light to travel through a periscope.

Figure 5:
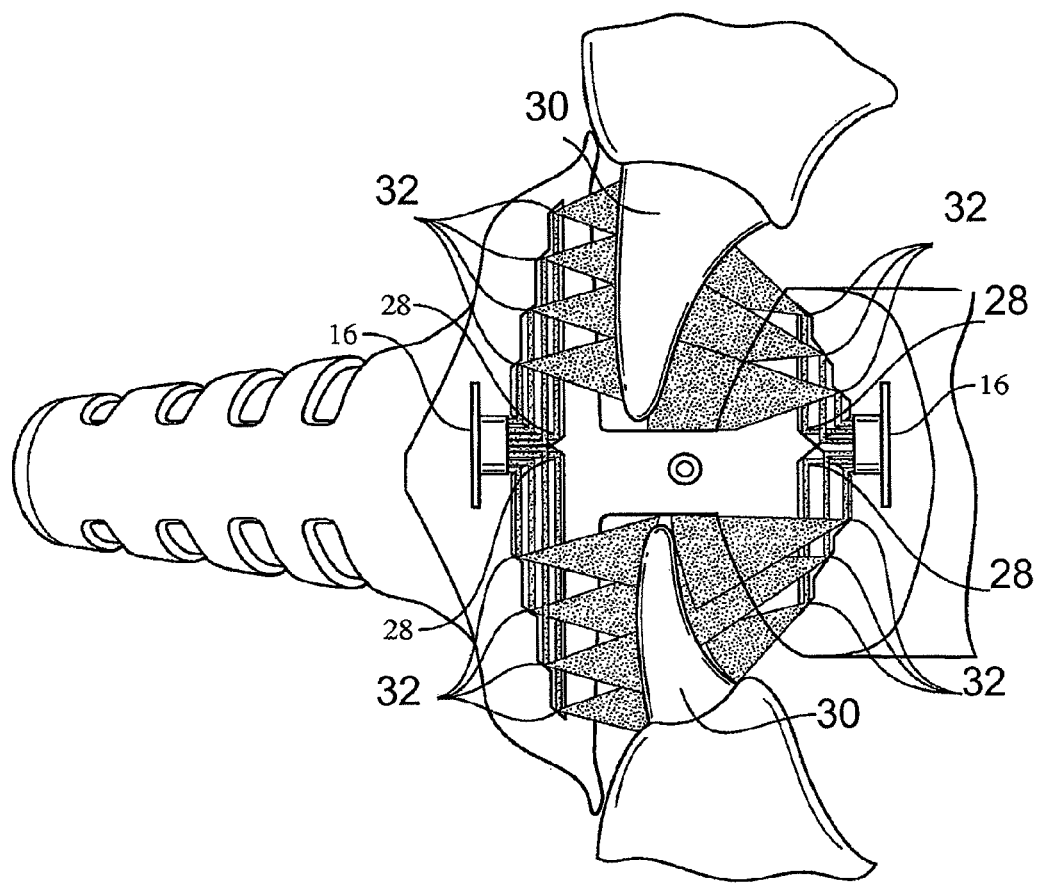
FIG. 5 is an isometric view of the flexible circuit board of the invention arranged in position on either side of incisor teeth.
Figure 6:
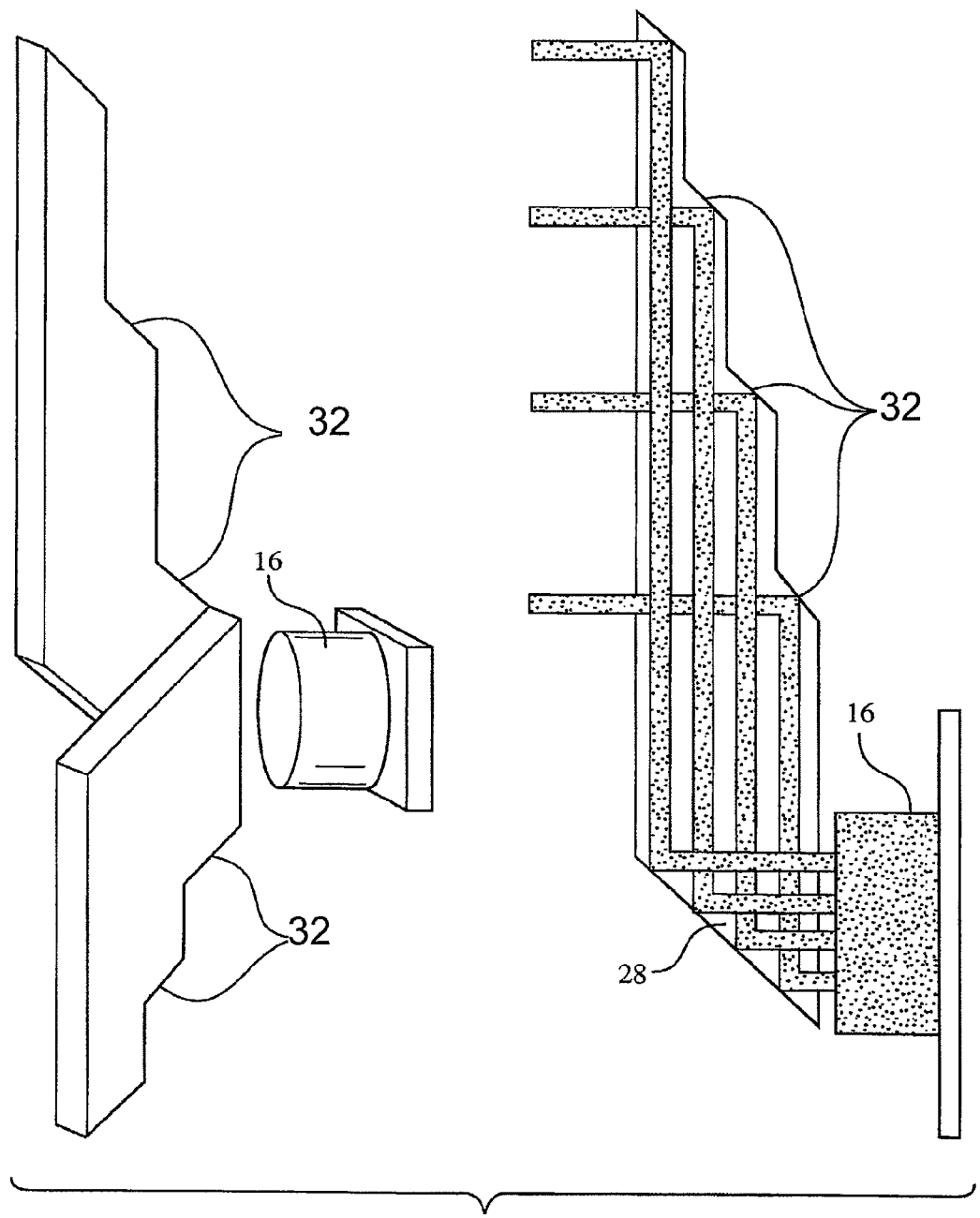
FIG. 6 is a schematic representation of a light emitting diode (LED), which is powered through the flexible circuit board of the invention, to direct light at a reflector, which reflects light emitted from the LED.

FIG. 5 shows "periscope" features molded as an over-molded insert to direct light to upper and lower incisor teeth. Staged or stepped, emitting reflectors 32 extend the area covered by reflecting light from light emitting diodes toward tooth surfaces. FIG. 6 shows an LED lamp 16 emitting its light at an angled mirror reflector 28, which reflects light toward the staged or stepped, emitting reflectors 32, which in turn reflects the light at tooth surfaces of incisors to be treated (e.g., whitened). The reflector 32 is angled to direct the reflected light away from the LED lamp 16.

Figure 7:
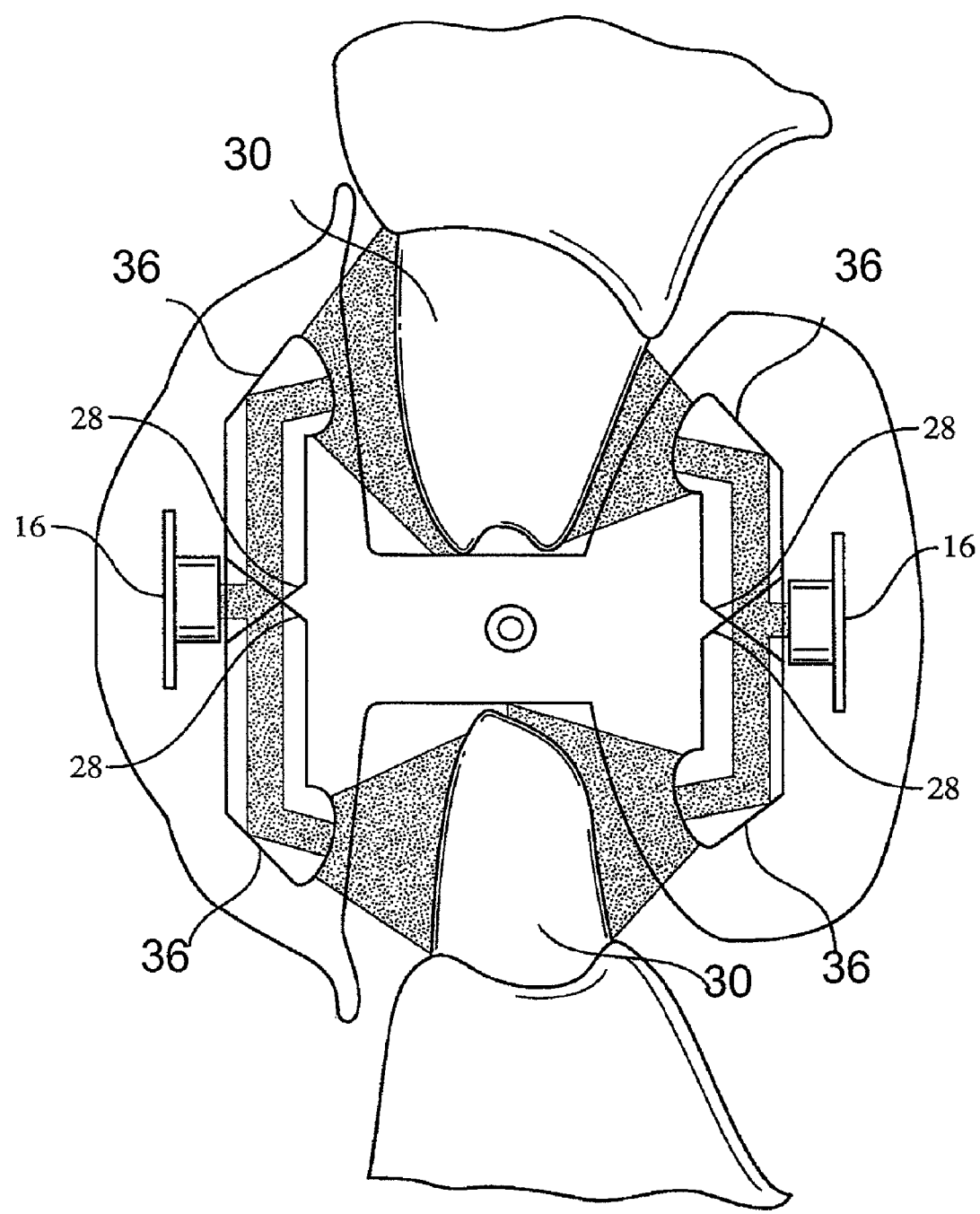
FIG. 7 is a plan view of the flexible circuit board of the invention in position on either side of canine/premolar teeth.

FIG. 7 shows another approach. "Periscope" features are molded as an over-molded insert. Distal lensing 36 extend the area covered by the light emission from LED lamps 16. Light emitted from the LED lamps 16 strike mirror reflectors 28, which reflect the light to the distal lensing 36, which in turn reflects the light toward surfaces of canine/premolar teeth.

Figure 8:
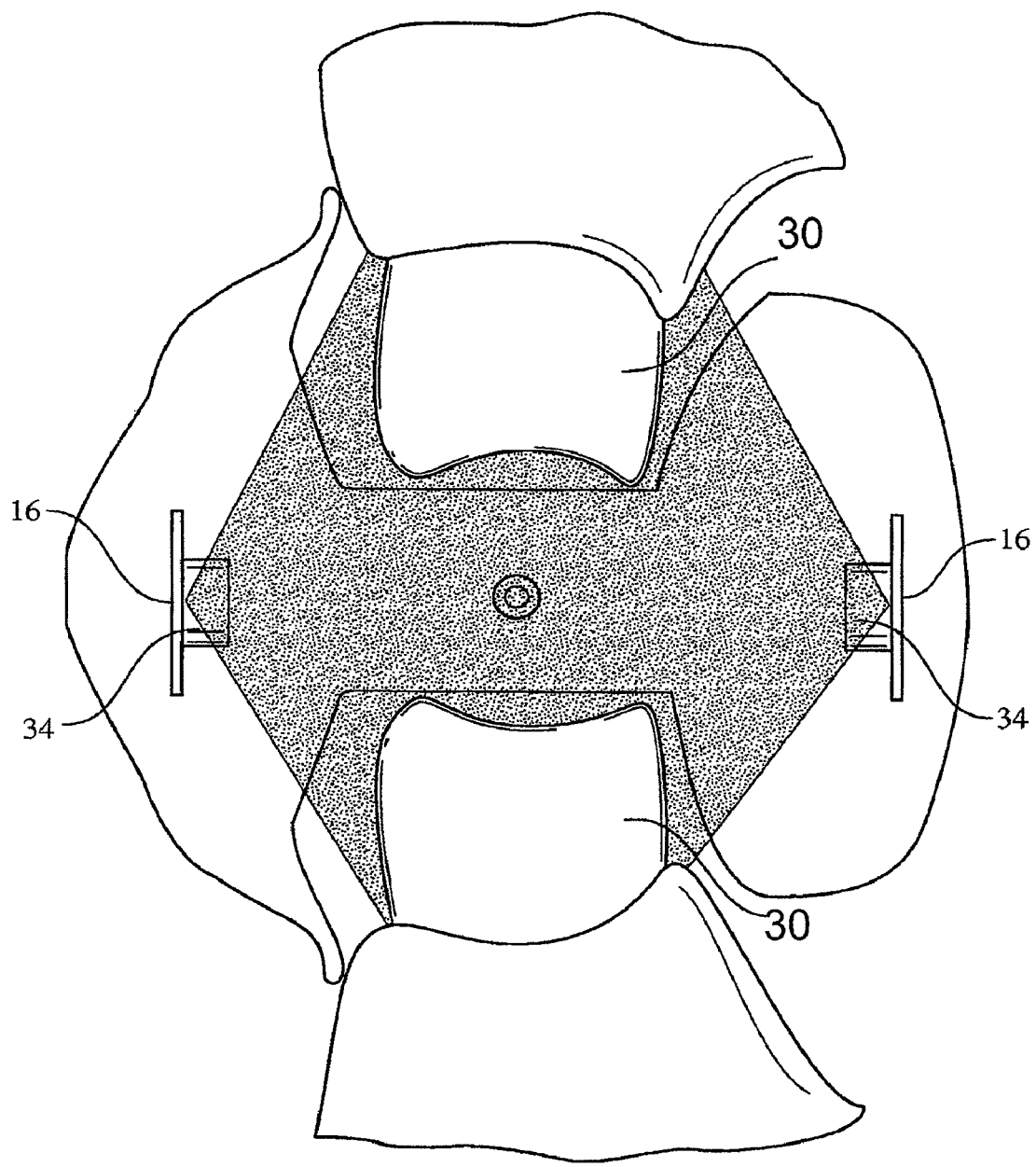
FIG. 8 is a plan view of the flexible circuit board of the invention in position on either side of molar teeth.

FIG. 8 shows yet another approach. A standard 120 degree emission LED lamps 16 are provided, with lensing 34 molded into the elastomer. Light from the LED lamps 16 is directed at the lensing 34, which directs the light at tooth surfaces of molars.

A specific application of the device in accordance with the invention is in a method to prevent periodontal disease, a disease of the gums caused by bacteria. In this method, a substance containing hydrogen peroxide from about 0.01% up to about 5%, or from about 0.05% to about 5%, is applied to the gums and then an oral treatment in accordance with the invention is effected. Such a substance may be a 1% hydrogen peroxide. This substance is designed to be heat and/or light-activated either alone or in combination with optional and additional heat and/or light initiating materials. After the substance is applied to the gums and the mouthpiece 22 is placed into the person's mouth in the manner described above, the combination of hydrogen peroxide and the heat and/or light-activated materials activated by the lamps 16 will oxygenate gum tissues thus killing gram negative anaerobic bacteria that cause gum disease (periodontal disease). Antioxidants may also be included in the substance for soft tissue health.

Traditionally, the only way to effectively remove gum disease-causing bacteria was to mechanically lift the bacteria from the space between the root surface and the gum tissue. This is done by the mechanical action of flossing, and/or by using an interdental brush which lifts and pushes the bacteria out of the space. However, it was found that only about 10% of the population flosses regularly and further, that about 65% of the population great than age 35 has some form of gum disease. Thus, there is a significant need for an easy, convenient way to eliminate the anaerobic bacteria (which live under the gum without oxygen). The intra-oral device 20 in accordance with the invention will, after hydrogen peroxide is applied to the gums, activate the oxygen in the hydrogen peroxide to penetrate under the gums and therefore will have an enhanced effect of killing the gum disease-causing bacteria (bad bacteria).

Instead of hydrogen peroxide, other substances that oxygenate gum tissues when subjected to heat and/or light may be applied to the teeth, and effect a similar gum disease prevention treatment using the intra-oral device 20 in accordance with the invention.

For example, the substance applied to the gums may be in the form of a gel that is in a highly viscous or lower viscosity liquid form that contains actives, i.e., activating compounds, that will target the gum disease-causing bacteria and allow healthy bacteria to live. This targeting of specific bacteria allows for the necessary bacterial balance to keep the homeostasis that is critical for overall health in the mouth.

Yet another dental treatment application of the intra-oral device 20 in accordance with the present invention is for desensitizing teeth. Tooth sensitivity occurs by the gingiva receding off of the tooth surface and thus exposing the root areas/surfaces of the tooth. These areas have small dentinal tubules that are filled with fluid that originate near the pulp of the tooth and are prone to excitation by certain stimuli of air and cold temperatures. A traditional method to desensitize teeth is to use a toothpaste or dentifrice that contains potassium nitrate and fluoride which seals the tubules and prevents the transmission of the stimulus to the root surface of the tooth.

However, in a method for desensitizing teeth using the intra-oral device 20 in accordance with the invention, a substance containing fluoride and/or potassium nitrate is applied to the teeth, and then the person puts the mouthpiece 22 into their mouth and activates the lamps 16. When activated by light and heat generated by the lamps 16, in the manner described above, the substance causes an increased uptake of fluoride ions and/or potassium nitrate which acts to seal the dentinal tubules. Today, fluoride and potassium nitrate are used in toothpaste to help prevent root sensitivity. However, the user has to brush with this dentifrice multiple times to see a long term effect. With the intra-oral device 20 in combination with this substance, the efficacy of the uptake of these actions is greatly enhanced with the user seeing a much quicker response to desensitizing the root surfaces. The substance can be in the form of a liquid or a gel that can have thixotropic properties that allows for the targeting of the substance onto the exposed root surface with the light and/or heat of the intra-oral device 20.

The present invention thereby provides methods and devices for treating teeth and gums by applying various substances to teeth and/or gums followed by a dental care routine involving the easy application of light and/or heat to the substance, e.g., desensitizing gel, stain and plaque removal and whitening gel. Disadvantages of prior art devices used for dental care are avoided.

While the foregoing description and drawings represent the preferred embodiments of the present invention, it will be understood that various changes and modifications may be made without departing from the spirit and scope of the present invention.

What is claimed is:

1. A method for effecting an oral treatment, comprising:
applying a substance to teeth or gums of a user's mouth;
providing a mouthpiece having a curvature, a flexible circuit board within confines of the mouthpiece and curved to follow the curvature of the mouthpiece, and a plurality of arrays of lamps electrically connected to the flexible circuit board, the arrays being interconnected and spaced from each other by a flexible strip at a generally central location of each array and the circuit board is folded or flexed at the central strip such that respective ones of lamps in a first of said arrays face respective ones of lamps in a second of said arrays, the lamps being configured to emit electromagnetic radiation when activated;
inserting the mouthpiece into the user's mouth after the substance has been applied to the teeth or gums; and
activating the lamps to emit electromagnetic radiation causing or increasing a reaction between the substance applied to the teeth or gums and the teeth or gums, said lamps directing said electromagnetic radiation on facial and lingual surfaces of said teeth or gums.

2. The method of claim 1, wherein the substance is an adhesive whitening gel such that the method is a method for whitening teeth.

3. The method of claim 2, wherein the step of applying the substance to the teeth comprises applying the adhesive whitening gel in a position in which it is exposed to the electromagnetic radiation from at least some of the lamps.

4. The method of claim 1, wherein the substance is a tooth desensitizing substance such that the method is a method for desensitizing teeth.

5. The method of claim 4, wherein the step of applying the substance to the teeth comprises applying the substance in a position in which it is exposed to the electromagnetic radiation from at least some of the lamps.

6. The method of claim 1, wherein the substance contains hydrogen peroxide, further comprising constructing the lamps to emit ultraviolet light as the electromagnetic radiation from the lamps to activate the oxygen in the hydrogen peroxide such that the method is a method for preventing periodontal disease.

7. The method of claim 6, wherein the step of applying the substance to the gums comprises applying the substance in a position in which it is exposed to the ultraviolet light from at least some of the lamps.

8. The method of claim 1, further comprising enabling the user to select, using a user interface, a plurality of light intensities that the lamps are to radiate during their operation.

9. The method of claim 8, further comprising enabling the user to adjust, using the user interface, an amount of heat to be generated by the lamps during their operation.

10. The method of claim 8, further comprising providing the user interface as a unit spaced away from the mouthpiece.

11. The method of claim 8, further comprising incorporating the user interface into a headset.

12. The method of claim 1, further comprising:
providing the mouthpiece with an H-shaped cross-section; and
arranging one of the arrays of lamps on each side of the H-shaped cross-section.

13. The method of claim 12, wherein the step inserting of the mouthpiece into the user's mouth comprises positioning the mouthpiece such that the user's teeth are in recessed portions between the sides of H-shaped cross-section.

14. The method of claim 1, further comprising arranging the mouthpiece such that the lamps are spaced from each other within the arrays.

15. The method of claim 1, further comprising orienting the lamps in the arrays such that the lamps of each array direct heat and/or light in a direction toward the other array.

16. The method of claim 1, further comprising arranging angled reflectors in a path of electromagnetic radiation emission from the lamps to divert the electromagnetic radiation emission toward staged reflectors, which in turn reflect the electromagnetic radiation emission.

17. The method of claim 1, further comprising arranging angled reflectors in a path of electromagnetic radiation emission from the lamps to divert the electromagnetic radiation emission toward distal lensing, which in turn reflect the electromagnetic radiation emission.

18. The method of claim 1, further comprising:
   encapsulating the lamps with an elastomer; and
   arranging lensing in the elastomer to angle emitted electromagnetic radiation from the lamps.

19. The method of claim 1, further comprising constructing the lamps to provide electromagnetic radiation in a range of 300-900 nm and to give off heat in an amount that is less than about 52 degrees Centigrade.

* * * * *